US00PP28655P3

(12) United States Plant Patent
Carruth

(10) Patent No.: US PP28,655 P3
(45) Date of Patent: Nov. 21, 2017

(54) GROUND COVER ROSE PLANT NAMED 'WEKSURDICLA'

(50) Latin Name: *Rosa hybrida*
Varietal Denomination: WEKsurdicla

(71) Applicant: Early Morning LLC, Lawrenceburg, IN (US)

(72) Inventor: Thomas F. Carruth, Altadena, CA (US)

(73) Assignee: Early Morning LLC, Lawrenceburg, IN (US)

( * ) Notice: Subject to any disclaimer, the term of this patent is extended or adjusted under 35 U.S.C. 154(b) by 21 days.

(21) Appl. No.: 14/757,119

(22) Filed: Nov. 20, 2015

(65) Prior Publication Data

US 2017/0150661 P1 May 25, 2017

(51) Int. Cl.
*A01H 5/02* (2006.01)

(52) U.S. Cl.
USPC ..... Plt./101

(58) Field of Classification Search
USPC ..... Plt./101
See application file for complete search history.

(56) References Cited

U.S. PATENT DOCUMENTS

PP10,240 P 2/1998 Ilsink
PP23,455 P2 3/2013 Carruth et al.

OTHER PUBLICATIONS

"HelpMeFind"—'Weksurdicla' website—http//www.helpmefind.com/gardening/l.php?i=2.72447 Retieved from the Internet on Jan. 31, 2017. (1 page total).*

* cited by examiner

*Primary Examiner* — Susan McCormick Ewoldt
(74) *Attorney, Agent, or Firm* — McKee, Voorhees & Sease, PLC

(57) ABSTRACT

A new variety of Ground Cover rose suitable for garden decoration, having flowers of yellow edged pink coloration.

1 Drawing Sheet

Classification: The present invention relates to a new *Rosa hybrida* plant.

Variety denomination: The new plant has the varietal denomination 'WEKsurdicla'.

BACKGROUND OF THE INVENTION

This invention relates to a new and distinct variety of Ground Cover Rose. It has as its seed parent the variety known as 'INTerdust' (U.S. Plant Pat. No. 10,240) and as its pollen parent the variety known as 'WEKfunk' (U.S. Plant Pat. No. 23,455).

SUMMARY OF THE INVENTION

Among the features which distinguish the new variety from other presently available and commercial rose cultivars known to the inventor are the following combinations of characteristics: its low spreading growing habit, its unusual for the class yellow edged pink flowers coloration and its medium flowers size for the class. The plant has a low spreading growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKsurdicla' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, 'INTerdust' by the following combination of characteristics: whereas 'WEKsurdicla' bears double flowers (about 20 to 30 petals) of yellow edged pink coloration, 'INTerdust' bears single to semi-double flowers of light yellow coloration with significantly lesser petalage (about 5 to 10 petals). The new variety bears medium sized flowers (about 5.5 to about 7.5 cm. in diameter), whereas the seed parent bears significantly smaller flowers (about 3.8 cm. in diameter).

The new variety may be distinguished from its pollen parent, 'WEKfunk' by the following combination of characteristics: whereas 'WEKsurdicla' bears medium sized flowers (about 5.5 to about 7.5 cm. in diameter) of yellow edged pink coloration, 'WEKfunk' bears significantly larger flowers (about 8.0 to about 10.6 cm. in diameter) of cream and cherry blushed burgundy coloration. The new variety has a spreading low growing habit (about 48 to about 66 cm. in height), whereas the pollen parent has an upright significantly taller growing habit (about 180 to about 200 cm. in height).

COMPARISON WITH THE CLOSEST COMMERCIALLY AVAILABLE CULTIVAR

The new variety may be distinguished from its closest commercially available cultivar, 'INTERhappy' (U.S. Plant Pat. No. 19,646) by the following combination of characteristics: whereas 'WEKsurdicla' bears double flowers (about 20 to 30 petals) of yellow edged pink coloration, 'INTERhappy' bears single flowers of yellow-orange coloration with significantly lesser petalage (6 petals under normal conditions). The new variety bears medium sized flowers (about 5.5 to about 7.5 cm. in diameter), whereas the closest commercially available cultivar bears significantly smaller flowers (average open diameter is about 4 cm).

BRIEF DESCRIPTION OF ILLUSTRATION

The accompanying photograph illustrates the new variety and shows the flowering thereof from bud to full bloom depicted in color as nearly correct as it is possible to make in a color illustration of the character. The branches used for the photograph came from 3 to 4 year-old rose plants of the new variety grown outdoors in Wasco, Calif. in the month of November. Throughout this specification, color references and/or values are based upon The Colour Chart of The Royal Horticultural Society (2001) except where common terms of color definition are employed.

DESCRIPTION OF THE NEW VARIETY

The following description is of 3 to 4 year-old rose plants of the new variety grown outdoors in Wasco, Calif. in the month of November. Phenotypic expression may vary with environmental, cultural and climatic conditions, as well as differences in conditions of light and soil.

FLOWER

The new variety usually bears its flowers in clusters of three to five or more per stem. Flowers are borne in rounded to somewhat pyramidal clusters on strong medium length to long stems (about 18 to about 35 cm.). The cluster ranges from about 9.3 to about 11.8 cm. in diameter. Outdoors, the plant blooms abundantly and nearly continuously during the growing season. The flowers have a mild tea to fruity fragrance.

BUD

The peduncle is about 3.5 to about 4.5 cm. in length, of slender caliper (about 0.2 to about 0.3 cm. in diameter), and usually erect to somewhat stiff. It is almost entirely rough, with many stipitate glands and a few small prickles. Peduncle color is between 146B and 146C often heavily suffused, especially on the side exposed to the sun, with between 183A and 183B.

Before the calyx breaks, the bud is about 1.3 to about 1.5 cm. in diameter at the widest point, about 0.8 to about 1.1 cm. in length, and pointed to somewhat ovoid in shape. The surface of the bud bears between 8 to 12 foliaceous appendages with many stipitate glands, usually with slender foliaceous parts extending beyond the tip of the bud about ¾ or more of its length. Bud color is between 146A and 146C often heavily suffused, especially on the side exposed to the sun, with between 183A and 183C.

The sepals are about 1.8 to about 2.3 cm. in length and about 0.6 to about 0.9 cm. in width at the widest point. The outer surface color of the sepal is between 146A and 146C often heavily suffused, especially on the side exposed to the sun, with between 183A and 183C. The outer surface of the sepal is moderately rough and bears between 0 to 4 foliaceous appendages with some stipitate glands and hairs. The inner surface color of the sepal is near 146C broadly bordered by near 137B. The inner surface of the sepal is covered with fine wooly tomentum; sepal margins are lined with many stipitate glands and numerous hairs.

The receptacle of the flower is somewhat short (about 0.6 to about 0.8 cm.) and somewhat thin to average in caliper (about 0.9 to about 1.2 cm. in diameter). The receptacle is funnel shaped in form. Its surface is smooth with somewhat thin fleshy walls. The receptacle color is between 137A and 137C.

As the petals open (after the calyx breaks), the bud is about 1.5 to about 1.7 cm. in diameter at the widest point, about 1.9 to about 2.3 cm. in length, and pointed to ovoid in form. The color of the under surfaces of the newly opened petals is between 16C and 15A blushed with between 46A to 46C. At the point where the petal attaches, there is a small zone of between 2A and 2C. The color of the upper surfaces of the newly opened petals is between 9A and 9B edged with between 53A to 53B. At the point where the petal attaches, there is a very small zone of between 13A and 13B.

BLOOM

When fully open, the bloom ranges from about 5.5 to about 7.5 cm. in diameter. Petalage is double with about 20 to 30 petals and about 1 to 5 petaloids irregularly arranged. When partially open, the bloom form is cupped to globular, and the petals are cupped with petal edges moderately reflexed inward to sometimes somewhat reflexed outward. When fully open, the bloom form is more cupped, and the petals are imbricated to cupped with petal edges moderately reflexed inward to sometimes somewhat reflexed outward.

PETALS

The substance of the petals is moderately heavy and of medium thickness, with upper surfaces slightly shiny and under surfaces matte. The petals are about 2.8 to about 3.5 cm. in length and about 1.9 to about 2.5 cm. in width at the widest point. Petal margins are entire.

The outer petals are oval to obovate in shape with rounded apices and sometimes notched with one notch.

The inner petals are oval to obovate in shape with rounded apices and sometimes notched with one notch.

Petaloids are about 0.5 to about 2.0 cm. in length and about 0.3 to about 0.5 cm. in width at the widest point. Petaloids are shaped somewhat gladiate to spatulate with mucronate to acuminate apices.

NEWLY OPENED FLOWER

The under surface color of the outer petals is between 4D and 13D. Toward the middle of the petal the base color is suffused with between 65C to 65D. At the point where the petal attaches, there is a small zone of near 1C. The upper surface color of the outer petals is between 9B and 8C. This color diffuses into between N66C to 67C toward the petal margins. At the point where the petal attaches, there is a small zone of between 14B and 14C.

The under surface color of the intermediate and inner petals is between 4D and 13D diffusing into between 65D to 65B. The upper surface color of the intermediate and inner petals is near 4C at the petal base diffusing to near N155D before changing to between N66C to 67B toward the petal margins.

The under and upper surface colors of the petaloids are similar in coloration to the upper and under surfaces of the intermediate and inner petals.

The general tonality of the newly opened flower is near 4C at the petal base diffusing to near N155D before changing to between N66C to 67B toward the petal margins.

THREE-DAY-OLD FLOWER

The upper surface color of the outer petals is between N66B and N66C with streaks of near N155C. At the point where the petal attaches, there is a small zone of between 14B and 14C. The under surface color of the outer petals is between 4D and 13D at the base of the petals changing to between 65C to 65D towards the petal edges. At the point where the petal attaches, there is a small zone of near 1C.

The under surface color of the intermediate and inner petals is between 4D and 13D diffusing to between 65D to 65B. The upper surface color of the intermediate and inner petals is between 9B and 8C diffusing to between N66C and 67C.

The under and upper surface colors of the petaloids are similar in coloration to the upper and under surfaces of the intermediate and inner petals.

The general tonality of the three-day-old flower is between 9B and 8C diffusing to between N66C and 67C.

On the spent bloom, the petals usually drop off cleanly.

In November in Wasco, Calif., blooms on the bush growing outdoors generally last about three to four days. Cut roses from plants grown outdoors and kept at normal indoor living temperatures generally last about four to five days.

MALE REPRODUCTIVE ORGANS

Stamens are many in number (average about 120) and are arranged regularly about the pistils; a few are mixed with petaloids. The filaments are of medium length (about 0.3 to about 0.9 cm.) most with anthers. Filaments are between 12A and 12C in color. The anthers are of medium size for the class and all open approximately at the same time. Anther color when immature is near 17B on the external part and near 16C on the internal part. Anther color at maturity is near 163A on the external part and near 200D on the internal part. Pollen is moderate to abundant and between 22B and 21D in color.

FEMALE REPRODUCTIVE ORGANS

Pistils vary in number (average about 60). The styles are somewhat uneven, moderately short in length (about 0.3 to about 0.5 cm.), thin in caliper, and loosely bunched. Stigma color is between 159A and 158D. Style color is between 53B to 53C. Ovaries are usually all enclosed in the calyx.

Hips have not been observed on this variety when grown in Wasco, Calif.

FOLIAGE

The compound leaves are usually comprised of three to five to occasionally seven leaflets and are borne abundantly. The five-leaflet leaves are about 5.5 to about 8.5 cm. in length and about 4.5 to about 5.5 cm. in width at the widest point, leathery in texture on both sides, and glossy in finish on the upper side and matte on the underside. The leaves have a pinnate venation pattern. The terminal leaflets are about 2.7 to about 3.7 cm. in length and about 1.5 to about 2.2 cm. in width at the widest point, shaped ovate with mostly acute to subacute apices and rounded bases. Their margins are simply serrate.

The upper surface color of the mature leaf is between 139A and 136A. The under surface color of the mature leaf is between 146A and 147B. The under and upper colors of the leaf veins on the mature leaf are similar in coloration to the upper and under surfaces colors of the mature leaf. The upper surface color of the young leaf is between 146A and 147B, often moderately suffused with between 183B and 178A. The under surface color of the young leaf is between 146B and 146C, often moderately suffused with between 183B and 178B. The under and upper colors of the leaf veins on the young leaf are similar in coloration to the upper and under surfaces colors of the young leaf.

The rachis is somewhat light in caliper and moderately rough. The upper side is deeply grooved with many stipitate glands on the edges of the grooves. The underside of the rachis is moderately rough with few stipitate glands and small prickles. The rachis color is near 137D on the underside and near 146A on the upper side, sometimes moderately suffused on the young leaves with between 187B to 183A.

The stipules are about 0.6 to about 0.9 cm. in length and moderately narrow (about 0.2 to about 0.4 cm.) with long straight points that usually turn out at an angle of more than 45 degrees. The under and upper surface color of the stipule is between 146A and 137C often moderately suffused on the young leaf with between 187B and 183A. The upper and under surfaces of the stipules are smooth in texture.

The petiole is light in caliper and moderately rough. The upper side is deeply grooved with many stipitate glands on the edges of the grooves. The underside of the petiole is moderately rough with few stipitate glands and small prickles. The petiole is about 0.6 to about 1.0 cm. in length and about 0.1 to about 0.15 cm in width at the widest point. The petiole color is near 137D on the underside and near 146A on the upper side, sometimes moderately suffused on the young leaves with between 187B to 183A.

The plant displays an above average degree of resistance to powdery mildew (*Sphaerotheca pannosa*) and rust (*Phragmidium* sp.) as compared to other commercial varieties grown under comparable conditions in Wasco, Calif. The plant's winter hardiness and drought/heat tolerance are yet to be determined.

GROWTH

The plant has a spreading low growing habit (about 48 to about 66 cm. in height and about 122 to about 195 cm. spread at the widest point), with full branching. It displays somewhat vigorous growth and the canes are of light to medium size caliper for the class (about 0.2 to about 0.5 cm. in diameter at the widest point).

The color of the major stems is between 146C and 138B. The major stems are rough in texture and they bear many large prickles that are about 0.5 to about 0.7 cm. in length. The large prickles are hooked slightly downward with a medium length oval base; prickle color is near 183A. The major stem bears many small prickles of similar shape and coloration.

The color of the branches is between 146C and 138B. The branches are rough in texture and they bear many large prickles which are of similar size and shape to the large prickles on the major stems; prickle color is near 183A. The branches bear many small prickles of similar shape and coloration.

The color of the new shoots is between 146B and 138B often heavily suffused with between 183A and 187B. The new shoots are rough in texture and they bear many large prickles which are of similar size and shape to the large prickles on the major stems; prickle color is near 183A. The shoots bear many small prickles of similar shape and coloration.

The invention claimed is:

1. A new and distinct Ground Cover rose plant of the variety substantially as described and illustrated herein.

* * * * *

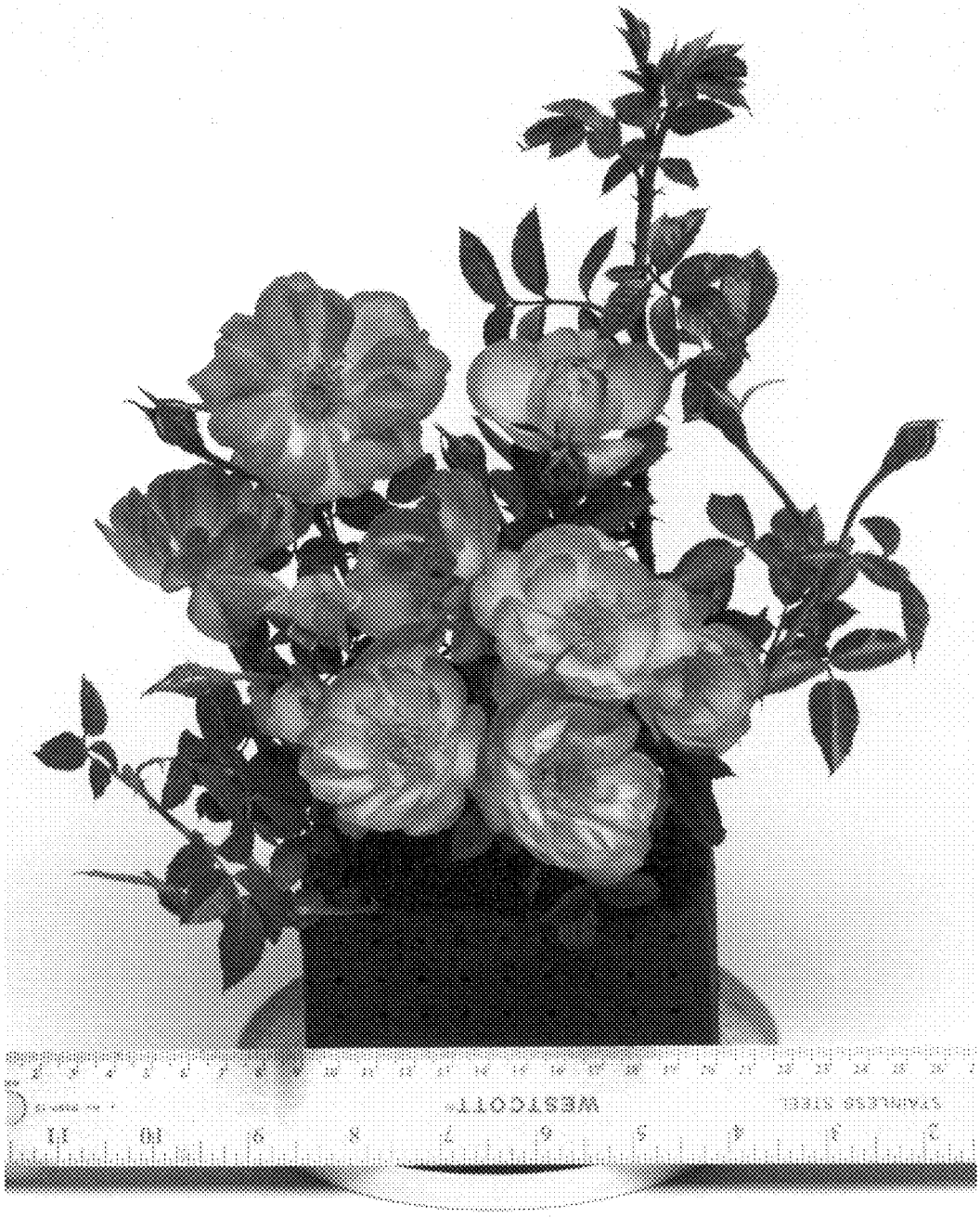
WESTCOTT
STAINLESS STEEL